United States Patent [19]

Blizzard et al.

[11] Patent Number: 4,923,867
[45] Date of Patent: May 8, 1990

[54] SYNTHETIC MARCFORTINE DERIVATIVES USEFUL AS ANTIPARASITIC AGENTS

[75] Inventors: Timothy A. Blizzard, Rahway; Helmut Mrozik, Matawan, both of N.J.

[73] Assignee: Merck & Co., Inc., Rahway, N.J.

[21] Appl. No.: 235,418

[22] Filed: Aug. 24, 1988

[51] Int. Cl.$^5$ .............. C07D 491/22; A61K 31/495; A01N 43/60
[52] U.S. Cl. ........................ 514/250; 544/230
[58] Field of Search ................... 544/230; 514/250

[56] References Cited
PUBLICATIONS

Polonsky et al., *Journal of the Chemical Society Chemical Communications* 1980, pp. 601–602.
Prange et al., *Tetrahedron Letters* 22, pp. 1977–1980 (1981).
Yamazaki et al., *Tetrahedron Letters* 22, pp. 135–136 (1981).

*Primary Examiner*—Mark L. Berch
*Attorney, Agent, or Firm*—David L. Rose; Hesna J. Pfeiffer

[57] ABSTRACT

There are disclosed synthetic marcfortine derivatives of the natural products marcfortine A, marcfortine B, and marcfortine C. The synthetic derivatives are described in the following formula:

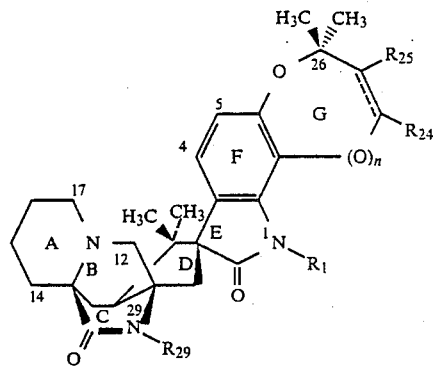

wherein:
n is 0 or 1
$R_1$ is hydrogen, loweralkyl, benzyl, lower alkanoyl, benzenesulfonyl in which the benzene ring is substituted with from 0 to 3 substituents selected from lower alkyl groups, lower alkoxy groups and halogen atoms, lower alkylamino-carbonyl, lower alkoxy-carbonyl;
$R_{24}$ is hydrogen, halogen or lower alkoxy (provided that $R_{24}$ is other than hydrogen only if the broken line represents a single bond at the 24, 25-position),
$R_{25}$ is hydrogen or halogen (provided that $R_{25}$ is other than hydrogen only if the broken line represents a single bond at the 24, 25-position);
$R_{29}$ is hydrogen, lower alkyl, alkoxyalkyl, haloalkyl, lower alkenyl, lower alkynyl, benzyl, lower alkanoyl, substituted benzenesulfonyl, lower alkylamino-carbonyl, not hydrogen or methyl if $R_1$ is hydrogen; and the broken line represents a single or double bond between carbons 24 and 25.

The compounds are active antiparasitic agents useful in particular against insect and nematode pests, and compositions for that use are disclosed.

19 Claims, No Drawings

SYNTHETIC MARCFORTINE DERIVATIVES USEFUL AS ANTIPARASITIC AGENTS

BACKGROUND OF THE INVENTION

The marcfortines are known compounds and are disclosed by Polonsky et al in *Journal of the Chemical Society Chemical Communications* 1980 601–602 (Marcfortine A) and *Tetrahedron Letters* 1981 22 1977–1980 (Marcfortines B and C). The compounds are fungal metabolites of *Penicillium roqueforti*. No uses for the compounds are suggested. The marcfortines are structurally related to paraherquamide and dihydroparaherquamide which are also known compounds Paraherquamide and dihydroparaherquamide- are disclosed by Yamazaki et al in *Tetrahedron Letters* 1981 22 135–136. Paraherquamide is a fungal metabolite of *Penicillium paraherquei*. Dihydroparaherquamide paraherquamide is prepared from paraherquamide by catalytic hydrogenation. No uses for the compounds are suggested. Marcfortine A has the following structure:

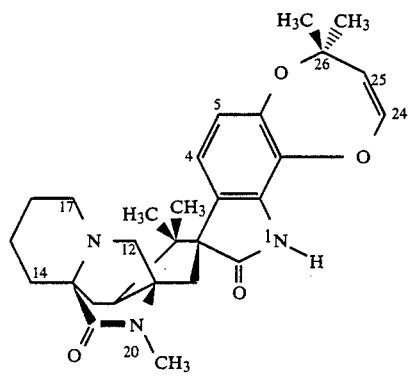

Marcfortine B has the following structure:

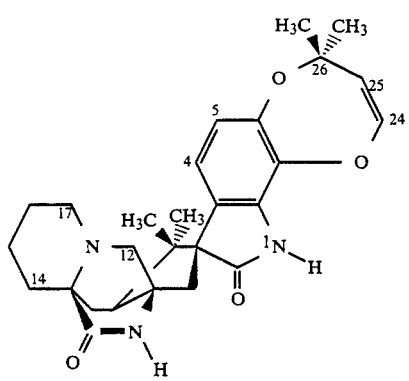

Marcfortine C has the following structure:

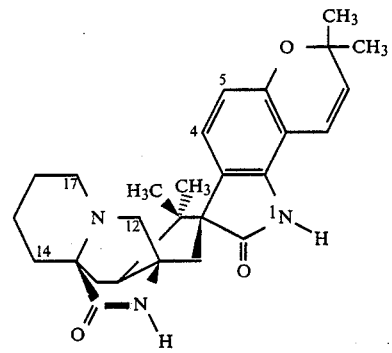

SUMMARY OF THE INVENTION

This invention is concerned with the synthesis of derivatives of the known marcfortines A, B, and C and the use of these derivatives as antiparasitic agents. Thus it is an object of this invention to describe these marcfortine derivatives. A further object of this invention is to describe processes for the preparation of these compounds. A still further object is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objects will become apparent from a reading of the following description.

DESCRIPTION OF THE INVENTION

The compounds of the instant invention are best realized in the following structure:

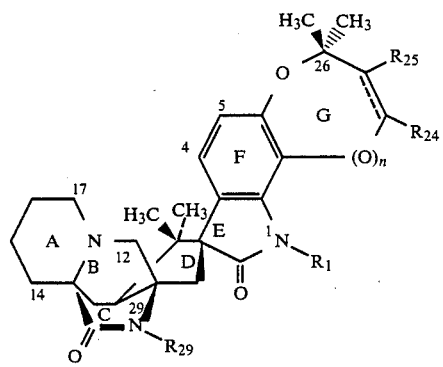

wherein:
n is 0 or 1
$R_1$ is hydrogen, lower alkyl, benzyl, lower alkanoyl, substituted benzenesulfonyl, lower alkylamino-carbonyl, lower alkoxy-carbonyl;
$R_{24}$ is hydrogen, halogen, lower alkoxy (provided that $R_{24}$ is other than hydrogen only if the broken line represents a single bond at the 24,25-position);
$R_{25}$ is hydrogen or halogen; (provided that $R_{25}$ is other than hydrogen only if the broken line represents a single bond at the 24,25-position);
$R_{29}$ is hydrogen, lower alkyl, alkoxyalkyl, haloalkyl, lower alkenyl, lower alkynyl, benzyl, lower alkanoyl, substituted benzenesulfonyl, lower alkylamino carbonyl, lower alkoxy carbonyl, except that $R_{29}$ is not hydrogen or methyl if $R_1$ is hydrogen; and the broken line represents a single or double bond between carbons 24 and 25.

In the instant invention "lower alkyl" is intended to include those alkyl groups of from 1 to 7 carbon atoms in either a straight or branched chain. Examples of such lower alkyl groups are methyl, ethyl, propyl, isopropyl, butyl, sec-butyl, pentyl, hexyl, heptyl, and the like.

The term "lower alkoxy" is intended to include those alkoxy groups of from 1 to 7 carbon to ms in either a straight or branched chain. Examples of such lower alkoxy groups are methoxy, ethoxy, propoxy, isopropoxy, butoxy, sec-butoxy, pentoxy, hexoxy, heptoxy, and the like.

The term "lower alkanoyl" is intended to include those alkanoyl groups of from 2 to 7 carbon atoms in either a straight or branched chain. Examples of such lower alkanoyl groups are acetyl, propionyl, butyryl, isobutyryl, pentanoyl, hexanoyl, and the like.

The term "alkoxyalkyl" is intended to include those lower alkoxy substituted lower alkyl groups containing from 2 to 8 carbon atoms and from 1 to 3 oxygen atoms in either a straight or branched chain. Examples of such alkoxyalkyl groups include methoxymethyl, methoxyethoxymethyl, methoxyethoxyethoxymethyl, ethoxyethyl, and the like.

The term "substituted benzenesulfonyl" is intended to include those benzenesulfonyl groups in which the benzene ring is substituted with from 0 to 3 substituents selected from lower alkyl groups, lower alkoxy groups and halogen atoms.

The term "halogen" is intended to include the halogen atoms fluorine, chlorine, bromine, and iodine.

The term "haloalkyl" is intended to include those halogen substituted lower alkyl groups containing from 1 to 7 carbon atoms in either a straight or branched chain and from 1 to 3 halogen atoms. Examples of such haloalkyl groups include fluoromethyl, bromoethyl, chloropropyl, iodopentyl, and the like.

The term "lower alkenyl" is intended to include those lower alkyl groups containing from 1 to 8 carbon atoms in either a straight or branched chain which contains 1 to 2 carbon double bonds. Examples of such lower alkenyl groups include allyl, butenyl, pentadienyl, hexenyl, and the like.

The term "lower alkynyl" is intended to include those alkynyl groups containing from 1 to 8 carbon atoms in either a straight or branched chain which contains 1 to 2 carbon-carbon triple bonds. Examples of such lower alkynyl groups include propargyl, butynyl, pentadiynyl, hexynyl and the like.

Preferred compounds of this invention are realized when:

n is 0 or 1

$R_1$ is hydrogen, lower alkyl, benzyl, lower alkanoyl, substituted benzenesulfonyl, lower alkylamino-carbonyl, lower alkoxy-carbonyl;

$R_{24}$ is hydrogen, halogen, or lower alkoxy (provided that $R_{24}$ is other than hydrogen only when the broken line represents a single bond at the 24,25 position);

$R_{25}$ is hydrogen or halogen (provided that $R_{25}$ is other than hydrogen only when the broken line represents a single bond at the 24,25 position);

$R_{29}$ is hydrogen, lower alkyl, alkoxyalkyl, haloalkyl, lower alkenyl, lower alkynyl, benzyl, lower alkanoyl, substituted benzenesulfonyl, lower alkylamino carbonyl, lower alkoxy carbonyl, except that $R_{29}$ is not hydrogen or methyl if $R_1$ is hydrogen; and the broken line represents a single or double bond between carbons 24 and 25.

More preferred compounds of this invention are realized when:

n is 1

$R_1$ is hydrogen, lower alkanoyl, substituted benzenesulfonyl;

$R_{24}$ is hydrogen or lower alkoxy (provided that $R_{24}$ is other than hydrogen when the broken line represents a single bond at the 24,25-position);

$R_{25}$ is hydrogen;

$R_{29}$ is hydrogen, lower alkyl, alkoxyalkyl, haloalkyl, lower alkenyl, lower alkynl, benzyl, lower alkanoyl, substituted benzenesulfonyl, except that $R_{29}$ is not hydrogen or methyl if $R_1$ is hydrogen; and the broken line represents a single or double bond between carbons 24 and 25. Still more preferred compounds of this invention are realized when:

n is 1

$R_1$ is hydrogen, substituted benzenesulfonyl;

$R_{24}$ is hydrogen;

$R_{25}$ is hydrogen;

$R_{29}$ is hydrogen, lower alkyl, alkoxyalkyl, haloalkyl, lower alkenyl, lower alkynl, benzyl, lower alkanoyl, substituted benzenesulfonyl, except that $R_{29}$ is not hydrogen or methyl if $R_1$ is hydrogen; and the broken line represents a double bond between carbons 24 and 25.

The most preferred compounds of this invention are realized when:

n is 1

$R_1$ is hydrogen;

$R_{24}$ is hydrogen;

$R_{25}$ is hydrogen;

$R_{29}$ is lower alkyl (except methyl), alkoxyalkyl, haloalkyl, lower alkenyl, lower alkynl, benzyl, lower alkanoyl, substituted benzenesulfonyl; and the broken line represents a double bond between carbons 24 and 25.

Examples of the preferred compounds of this invention are as follows:

24,25 dihydro-marcfortine A
24 propoxy-24,25-dihydro-marcfortine A
1-N (p toluenesulfonyl)-marcfortine A
1-N acetyl-marcfortine A
1-N-methyl marcfortine A
1-N benzyl-marcfortine A
1-N-dimethylcarbamoyl-marcfortine A
1-N-methoxycarbonyl-marcfortine A
24,25-dihydro-marcfortine B
24-methoxy-24,25-dihydro-marcfortine B
1-N-(p toluenesulfonyl)-marcfortine B
1-N-acetyl-marcfortine B
1-N-ethyl-marcfortine B
1-N-benzyl-marcfortine B
29-N-(p-toluenesulfonyl)-marcfortine B
29-N-acetyl marcfortine B
29-N-ethyl-marcfortine B
29-N benzyl-marcfortine B
29-N methoxyethoxymethyl marcfortine B
29-N-(3-chloropropyl) marcfortine B
29-N-allyl-marcfortine B
29-N-proparqyl marcfortine B
29-N ethyl-24 methoxy-24,25-dihydro-marcfortine B
1-N,29-N-bis (p-toluenesulfonyl)-marcfortine B
1-N,29-N bis acetyl-marcfortine B 1-N,29-N bis-ethyl-marcfortine B
1-N,29-N bis-benzyl marcfortine B
29-N-ethyl 24-methoxy 24,25-dihydro marcfortine B
1-N-(p-methoxybenzene sulfonyl) 29-N-ethyl 24-methoxy4,25 dihydro-marcfortine B
29-N-ethyl-24,25 dihydro-marcfortine B
24,25 dihydro-marcfortine C
1-N-(p bromobenzene sulfonyl)-marcfortine C
1-N-propionyl marcfortine C
1-N-propyl marcfortine C
1-N-benzyl-marcfortine C
29-N-(p-bromobenzene-sulfonyl)-marcfortine C
29-N-propionyl marcfortine C
29-N-propyl-marcfortine C
29-N-benzyl-marcfortine C
29-N-methoxyethoxymethyl-marcfortine C
29 N-(3-chloropropyl)-marcfortine C
29-N-allyl-marcfortine C
29 N-propargyl marcfortine C
1-N,29-N-bis-(p-bromobenzene-sulfonyl)-marcfortine C
1-N,29-N-bis-propionyl marcfortine C
1-N,29-N-bis-propyl-marcfortine C
1-N,29-N-bis-benzyl-marcfortine C The novel compounds of this invention are prepared by the following procedures:

A large series of marcfortine analogs can be prepared by alkylation or acylation of the free NH groups of the marcfortines. These derivatives may be easily prepared by sequential treatment of a solution of marcfortine A, marcfortine B, or marcfortine C in an aprotic organic solvent such as tetrahydrofuran, ether, benzene and the like with an excess of a strong base such as potassium hydride (preferred), sodium hydride, butyllithium, potassium tert-butoxide, and the like followed by a suitable alkylating or acylating agent at temperatures ranging from 0° C. to 50° C. for 0.25 to 48 hours. Suitable alkylating agents include alkyl bromides, alkyl iodides, alkyl sulfonates, alkenyl iodides, alkynyl bromides, alkoxyalkyl chlorides, and the like. Suitable acylating agents include acyl anhydrides, acyl chlorides, acyl bromides, substituted benzenesulfonyl chlorides, substituted benzenesulfonic anhydrides, isocyanates, carbamoyl chlorides, chloroformates, and the like. Treatment of marcfortine A under these conditions affords 1-N-substituted analogs which can be isolated and purified by using techniques known to those skilled in the art. When applied to marcfortine B or C this process affords a mixture of 1-N-substituted, 29-N substituted, and 1-N,29-N-bis-substituted marcfortine analogs which can be separated by silica gel chromatography. The individual components of the mixture can be isolated and purified by using techniques known to those skilled in the art.

An additional series of derivatives can be generated by modification of the G ring of marcfortines A, B and C. The 24,25 dihydro analogs are readily prepared by stirring a solution of the appropriate marcfortine in an alcoholic solvent such as methanol, ethanol, propanol and the like with a catalyst such as palladium, platinum, tris (triphenylphosphine)-chlororhodium and the like in the presence of hydrogen gas. The product, which is a 24,25-dihydro-marcfortine analog, can be isolated and purified by using techniques known to those skilled in the art. Note that the reactions described above for modification of other portions of the marcfortine structure may also be applied to 24,25-dihydro marcfortine analogs to prepare the corresponding 24-25,dihydro analogs, which are new compounds. Additional G ring modified analogs of the marcfortines may be prepared via the 24,25 dibromide which is easily prepared by treating a solution of a marcfortine in a halogenated solvent such as dichloromethane, chloroform, carbon tetrachloride and the like with 1 molar equivalent of bromine at temperatures ranging from −20° C. to 25° C. for 0.25 to 8 hours. This process affords the corresponding 24,25-dibromo 24,25-dihydro-marcfortine derivative which can be isolated and purified by using techniques known to those skilled in the art. Note that the 24,25 dichloro analog may be prepared by substituting chlorine for bromine in the process described above. The 24,25-dibromo 24,25-dihydro-marcfortine analogs described above are useful intermediates for the preparation of additional derivatives. Thus, treatment of a solution of the dibromide in an alcoholic solvent such as methanol, ethanol, propanol, and the like with a strong base such as 1,8-diazabicyclo[5.4.0]undec-7-ene (DBU) at temperatures ranging from 0° C. to 30° C. for 0.25 to 24 hours affords 24-alkoxy,25 bromo-24,25 dihydro-marcfortine analogs which can be isolated and purified by using techniques known to those skilled in the art. These 24 alkoxy,25-bromo derivatives can be debrominated by treatment of a solution of the compound in an aprotic organic solvent such as benzene, toluene, hexane, and the like with a tin hydride reducing agent such as tri butyl tin hydride, tri-phenyl tin hydride and the like with or without the addition of a radical initiator such as azobis-isobutyronitrile (AIBN) at temperatures ranging from 25° C. to 120° C. for 0.5 to 48 hours. This process affords the corresponding 24-alkoxy-marcfortine derivatives ($R_{24}$=lower alkoxy in the general structure) which can be isolated and purified by using techniques known to those skilled in the art.

PREPARATION OF STARTING MATERIALS

Marcfortines A, B and C are isolated, along with the previously known roquefortine, as fungal metabolites of *Penicillium roqueforti* using standard fermentation and isolation techniques. The isolation, as well as the analytical and structural characteristics of marcfortine A, are described in detail in Polonsky et al *Journal of the Chemical Society Chemical Communications* 1980 601–602. The isolation, as well as the analytical and structural characteristics of marcfortines B and C, are described in detail in Polonsky et al *Tetrahedron Letters* 1981 22 1977–1980.

From the extraction of 196 g of a lyophilized mycelium of the fermentation of *Penicillium roqueforti*, an alkaloidal extract of 280 mg is produced. Chromatography yields 24 mg of roquefortine, 79 mg of marcfortine A and marcfortines B and C.

The instant compounds of this invention are unexpectedly potent antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chahertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syohacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans. The instant compounds when administered orally or parenterally are administered at a dosage rate of from 0.05 to 20 mg/kg of animal body weight.

The instant compounds are also useful against common household pests such as *Blatella sp.* (cockroach), *Tineola sp.* (clothes moth), *Attagenus sp.* (carpet beetle), *Musca domestica* (housefly) and against *Solenopsis Invicta* (imported fire ant).

The compounds are furthermore useful against agricultural pests such as aphids (*Acyrthiosiphon sp.*), locusts, and boll weevils as well as against insect pests which attack stored grains such as *Tribolium sp.* and against immature stages of insects living on plant tissue. The compounds are also useful as a nematocide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, suspending agents, and/or binders such that a uniform mixture solution or suspension is obtained. An inert ingredient is one that will not react with the instant compounds and which is non toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.5 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.005 to 15 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention.

EXAMPLE 1

24,25 dihydro-marcfortine A

A mixture consisting of 15 mg of 5% palladium on carbon and marcfortine A (30 mg, 0.06 mmol) in 1 ml of methanol is stirred vigorously under an atmosphere of hydrogen for 45 minutes. The reaction mixture is filtered through Celite® and the filtrate is evaporated under vacuum. Preparative layer chromatography of the residue on a 0.5 mm silica gel plate eluted with 3% methanol in methylene chloride affords 24,25-dihydro marcfortine A which is identified by nuclear magnetic resonance and mass spectrometry.

EXAMPLE 2

24,25-dibromo-24,25-dihydro marcfortine A

A solution of bromine in chloroform (0.4 ml of 12M solution, 0.048 mmol) is added dropwise to a cold (ice bath) solution of marcfortine A (20 mg, 0.04 mmol) in 2 ml of chloroform. The resulting yellow solution is stirred at room temperature for 15 minutes then evaporated under a stream of nitrogen. Preparative layer chromatography of the residue on a 0.5 mm silica gel plate eluted with 2% methanol in methylene chloride affords 24,25-dibromo-24,25-dihydro-marcfortine A (mixture of stereoisomers at C-24 and C-25) which is identified by nuclear magnetic resonance and mass spectrometry.

EXAMPLE 3

24-methoxy 24,25-dihydro marcfortine B

A solution of bromine in chloroform (0.6 ml of 0.12M solution, 0.072 mmol) is added dropwise to a cold (ice bath) solution of marcfortine B (28 mg, 0.06 mmol) in 2 ml of chloroform. The resulting yellow solution is stirred at room temperature for 10 minutes then at 0 C for 20 minutes then evaporated under a stream of nitrogen. The yellow solid residue is dissolved in 2 ml of methanol then 1,8-diazabicyclo[5.4.0]undec-7-ene (DBU, 0.015 ml, 0.10 mmol) is added. The solution is stirred at room temperature for 90 minutes then evaporated under vacuum. Preparative layer chromatography of the residue on a 1.0 mm silica gel plate eluted with 2% methanol in methylene chloride affords a colorless oil which is identified by nuclear magnetic resonance and mass spectrometry as 24-methoxy-25 bromo-24,25-dihydro-marcfortine B. The 24-methoxy 25 bromo-24,25-dihydro-marcfortine B thus obtained is dissolved in 2 ml of dry toluene then tributyltin hydride (0.12 ml, 0.45 mmol) is added. The solution is stirred at 100° C. for 16 hours then evaporated under vacuum. Preparative layer chromatography of the residue on a 2.0 mm silica gel plate eluted with 2% methanol in methylene chloride affords 24-methoxy 24,25-dihydro-marcfortine B (mixture of stereoisomers at C 24) which is identified by nuclear magnetic resonance and mass spectrometry.

EXAMPLE 4

24-propoxy 24,25 dihydro-marcfortine A

Substitution of propanol for methanol in the procedure described above for 24-methoxy 24,25-dihydro-marcfortine B (EXAMPLE 3) and application of the modified procedure to 20 mg of marcfortine A affords an oily residue. Preparative layer chromatography of the crude product on a 0.5 mm silica gel plate eluted with 2% methanol in methylene chloride affords 24-propoxy-24,25-dihydro-marcfortine A (mixture of stereoisomers at C 24) which is identified by nuclear magnetic resonance and mass spectrometry.

EXAMPLE 5

29-N-ethyl-marcfortine B

Potassium hydride (80 mg of a 25% oil dispersion) is added to a solution of marcfortine B (28 mg, 0.060 mmol) in 2 ml of dry tetrahydrofuran. The solution is stirred at room temperature for 2 hours then iodoethane (0.0073 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N ethyl-marcfortine B, 1-N-ethyl-marcfortine B, and 1-N,29 N bis ethyl marcfortine B, is chromatographed on a 1.0 mm silica gel plate eluted twice with 20% acetone in hexane. Three bands are isolated and identified by nuclear magnetic resonance and mass spectrometry as 29 N-ethyl-marcfortine B, 1 N-ethyl-marcfortine B, and 1-N,29 N-bis ethyl-marcfortine B, respectively.

EXAMPLE 6

29 N benzyl marcfortine B

Potassium hydride (80 mg of a 25% oil dispersion) is added to a solution of marcfortine B (28 mg, 0.060 mmol) in 2 ml of dry tetrahydrofuran. The solution is stirred at room temperature for 2 hours then benzyl bromide (0.011 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29 N-benzyl-marcfortine B, 1-N-benzyl-marcfortine B, and 1-N,29 N-bis-benzyl-marcfortine B, is chromatographed on a 1.0 mm silica gel plate eluted twice with 20% acetone in hexane. Three bands are isolated and identified by nuclear magnetic resonance and mass spectrometry as 29 N benzyl-marcfortine B, 1-N-benzyl-marcfortine B, and 1N,29-N-bis-benzyl-marcfortine B, respectively.

EXAMPLE 7

1N benzyl-marcfortine A

Potassium hydride (75 mg of a 25% oil dispersion) is added to a solution of marcfortine A (15 mg, 0.030 mmol) in 1 ml of dry tetrahydrofuran. The solution is stirred at room temperature for 2 hours then benzyl bromide (0.025 ml, 0.21 mmol) is added. The mixture is stirred at room temperature for 3 hours then partitioned between water (1 ml) and methylene chloride (1 ml). The layers are separated and the aqueous layer extracted with methylene chloride (2 ml). The combined extracts are dried with magnesium sulfate, filtered, and evaporated under vacuum. Preparative layer chromatography of the residue on a 1.0 mm silica gel plate eluted with 3% methanol in methylene chloride affords 1 N-benzyl-marcfortine A which is identified by nuclear magnetic resonance and mass spectrometry.

EXAMPLE 8

1N-(dimethylcarbamoyl)-marcfortine A

Potassium hydride (50 mg of a 25% oil dispersion) is added to a solution of marcfortine A (15 mg, 0.030 mmol) in 1 ml of dry tetrahydrofuran. The solution is stirred at room temperature for 2 hours then dimethylcarbamyl chloride (0.028 ml, 0.30 mmol) is added. After 3 hours at room temperature an additional 0.25 ml of dimethylcarbamyl chloride is added. The mixture is stirred at room temperature for an additional 18 hours then partitioned between 5% aqueous sodium bicarbonate (1 ml) and methylene chloride (1 ml). The layers are separated and the aqueous layer extracted with methylene chloride (2 ml). The combined extracts are dried with magnesium sulfate, filtered, and evaporated under vacuum. Preparative layer chromatography of the residue on a 0.5 mm silica gel plate eluted with 25% acetone in hexane affords 1-N (dimethylcarbamoyl)-marcfortine A which is identified by nuclear magnetic resonance and mass spectrometry.

EXAMPLE 9

29-N-acetyl-marcfortine B

Potassium hydride (14 drops of a 25% oil dispersion) is added to a solution of marcfortine B (19 mg, 0.040 mmol) in 2 ml of dry tetrahydrofuran. The solution is stirred at room temperature for 2 hours then acetic anhydride (0.006 ml, 0.060 mmol) is added. The mixture is stirred at room temperature for 22 hours then partitioned between 5% aqueous sodium bicarbonate (2 ml) and methylene chloride (3 ml). The layers are separated and the aqueous layer extracted twice with methylene chloride (7 ml). The combined extracts are dried with magnesium sulfate, filtered, and evaporated under vacuum. The residue, consisting of a mixture of 29 N acetyl-marcfortine B, 1-N acetyl marcfortine B, and 1 N,29-N-bis acetyl-marcfortine B, is chromatographed on a 1.0 mm silica gel plate eluted twice with 2% methanol in methylene chloride. Three bands are isolated which are identified by nuclear magnetic resonance and mass spectrometry as 29-N-acetyl-marcfortine B, 1N acetyl-marcfortine B, and 1-N,29-N-bis-acetyl-marcfortine B, respectively.

EXAMPLE 10

29-N propionyl-marcfortine C

Potassium hydride (14 drops of a 25% oil dispersion) is added to a solution of marcfortine C (18 mg, 0.040 mmol) in 2 ml of dry tetrahydrofuran. The solution is stirred at room temperature for 2 hours then propionic anhydride (0.008 ml, 0.060 mmol) is added. The mixture is stirred at room temperature for 3 hours then partitioned between 5% aqueous sodium bicarbonate (2 ml) and methylene chloride (3 ml). The layers are separated and the aqueous layer extracted twice with methylene chloride (7 ml). The combined extracts are dried with magnesium sulfate, filtered, and evaporated under vacuum. The residue, consisting of a mixture of 29-N-propionyl-marcfortine C, 1-N-propionyl-marcfortine C, and 1-N,29-N-bis-propionyl-marcfortine C, is chromatographed on a 1.0 mm silica gel plate eluted twice with 2% methanol in methylene chloride. Three bands are isolated which are identified by nuclear magnetic resonance and mass spectrometry as 29-N propionyl-marcfortine C, 1-N-propionyl-marcfortine C, and 1-N,29-N-bis-propionyl-marcfortine C, respectively.

EXAMPLE 11

1-N-(methoxycarbonyl)-marcfortine A

Potassium hydride (20 drops of a 25% oil dispersion) is added to a solution of marcfortine A (25 mg, 0.051 mmol) in 3 ml of dry tetrahydrofuran. The solution is stirred at room temperature for 2 hours then methyl chloroformate (0.60 ml, 0.78 mmol) is added. The mixture is stirred at room temperature for 6 hours then partitioned between 5% aqueous sodium bicarbonate (2 ml) and methylene chloride (3 ml). The layers are separated and the aqueous layer extracted twice with methylene chloride (7 ml). The combined extracts are dried with magnesium sulfate, filtered, and evaporated under vacuum. Preparative layer chromatography of the residue on a 1.5 mm silica gel plate eluted with 2% methanol in methylene chloride affords 1-N-(methoxycarbonyl)-marcfortine A which is identified by nuclear magnetic resonance and mass spectrometry.

EXAMPLE 12

29-N-(p-toluenesulfonyl)-marcfortine B

Potassium hydride (60 mg of a 25% oil dispersion) is added to a solution of marcfortine B (14 mg, 0.030 mmol) in 1 ml of dry tetrahydrofuran. The solution is stirred at room temperature for 2 hours then p- toluenesulfonyl chloride (9 mg, 0.047 mmol) is added. The mixture is stirred at room temperature for 1 hour then partitioned between 5% aqueous sodium bicarbonate (1 ml) and methylene chloride (1 ml). The layers are separated and the aqueous layer extracted with methylene chloride (2 ml). The combined extracts are dried with magnesium sulfate, filtered, and evaporated under vacuum. The residue, which consists of a mixture of 29-N-(p-toluenesulfonyl)-marcfortine B, 1-N (p toluenesulfonyl)-marcfortine B, and 1-N,29-N-bis-(p toluenesulfonyl)-marcfortine B, is chromatographed on a 1.0 mm silica gel plate eluted with 3% methanol in methylene chloride. Three bands are isolated and identified by nuclear magnetic resonance and mass spectrometry as 29-N (p toluenesulfonyl) marcfortine B, 1-N-(p toluenesulfonyl) marcfortine B, and 1-N,29-N-bis (p-toluenesulfonyl) marcfortine B, respectively.

EXAMPLE 13

29-N-allyl-marcfortine C

Potassium hydride (80 mg of a 25% oil dispersion) is added to a solution of marcfortine C (27 mg, 0.060 mmol) in 2 ml of dry tetrahydrofuran. The solution is stirred at room temperature for 2 hours then allyl iodide (0.0082 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N-allyl-marcfortine C, 1-N allyl-marcfortine C, and 1-N,29-N-bis-allyl marcfortine C, is chromatographed on a 1.0 mm silica gel plate eluted twice with 20% acetone in hexane. Three bands are isolated and identified by nuclear magnetic resonance and mass spectrometry as 29-N-allyl-marcfortine C, 1-N-allyl-marcfortine C, and 1-N,29 N bis-allylmarcfortine C, respectively.

EXAMPLE 14

29-N-propargyl marcfortine B

Potassium hydride (80 mg of a 25% oil dispersion) is added to a solution of marcfortine B (28 mg, 0.060 mmol) in 2 ml of dry tetrahydrofuran. The solution is stirred at room temperature for 2 hours then propargyl bromide (0.008 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N propargyl-marcfortine B, 1-N-propargyl marcfortine B, and 1-N,29-N bis propargyl-marcfortine B, is chromatographed on a 1.0 mm silica gel plate eluted twice with 20% acetone in hexane. Three bands are isolated and identified by nuclear magnetic resonance and mass spectrometry as 29-N-propargyl-marcfortine B, 1-N-propargyl-marcfortine B, and 1-N,29-N bis propargyl-marcfortine B, respectively.

EXAMPLE 15

29-N (3 chloropropyl)-marcfortine B

Potassium hydride (80 mg of a 25% oil dispersion) is added to a solution of marcfortine B (28 mg, 0.060 mmol) in 2 ml of dry tetrahydrofuran. The solution is stirred at room temperature for 2 hours then 1 bromo 3-chloropropane (0.009 ml, 0.09 mmol) is added. The mixture is stirred at room temperature for 4 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N -(3 chloropropyl)-marcfortine B, 1-N-(3-chloropropyl)-marcfortine B, and 1-N,29-N-bis-(3-chloropropyl) marcfortine B, is chromatographed on a 1.0 mm silica gel plate eluted twice with 20% acetone in hexane. Three bands are isolated and identified by nuclear magnetic resonance and mass spectrometry as 29-N-(3-chloropropyl)-marcfortine B, 1-N-(3 chloropropyl)-marcfortine B, and 1-N,29-N-bis-(3 chloropropyl)-marcfortine B, respectively.

EXAMPLE 16

29-N-methoxyethoxymethyl-marcfortine B

Potassium hydride (80 mg of a 25% oil dispersion) is added to a solution of marcfortine B (28 mg, 0.060 mmol) in 2 ml of dry tetrahydrofuran. The solution is stirred at room temperature for 2 hours then 2-methoxyethoxymethyl chloride (MEM chloride, 0.010 ml, 0.09 mmol) is added. The mixture is stirred at room temperature for 5 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N-methoxyethoxymethyl-marcfortine B, 1-N-methoxyethoxymethyl-marcfortine B, and 1-N,29-N-bis-methoxyethoxymethyl-marcfortine B, is chromatographed on a 1.0 mm silica gel eluted twice with 30% acetone in hexane. Three bands are isolated and identified by nuclear magnetic resonance and mass spectrometry as 29-N-methoxyethoxymethyl-marcfortine B, 1-N-methoxyethoxymethyl-marcfortine B, and 1-N,29-N-bis-methoxyethoxymethyl marcfortine B, respectively.

EXAMPLE 17

29-N-ethyl 24-methoxy 24,25-dihydro marcfortine B

Potassium hydride (80 mg of a 25% oil dispersion) is added to a solution of 24-methoxy 24,25-dihydro-marcfortine B (see EXAMPLE 3, 30 mg, 0.060 mmol) in 2 ml of dry tetrahydrofuran. The solution is stirred at room temperature for 2 hours then iodoethane (0.0073 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml) The combined extracts are dried with magnesium sulfate, filtered, and evaporated under vacuum. The residual oil, consisting of a mixture of 29-N-ethyl-24-methoxy-24,25-dihydro-marcfortine B, 1-N-ethyl-24-methoxy-24,25-dihydro-marcfortine B, and 1-N,29-N-bis-ethyl-24-methoxy-24,25 dihydro-marcfortine B, is chromatographed on a 1.0 mm silica gel plate eluted twice with 20% acetone in hexane. Three bands are isolated and identified by nuclear magnetic resonance and mass spectrometry as 29-N ethyl-24 methoxy-24,25-dihydro-marcfortine B, 1-N ethyl-24-methoxy-24,25 dihydro-marcfortine B, and 1-N,29-N- bis ethyl-24-methoxy-24,25-dihydro marcfortine B, respectively.

EXAMPLE 18

1-N-(p-methoxy benzenesulfonyl)-29-N-ethyl-24 methoxy-24,25-dihydro-marcfortine B Potassium hydride (60 mg of a 25% oil dispersion) is added to a solution of 29-N-ethyl 24 methoxy-24,25-dihydro-marcfortine B (16 mg, 0.030 mmol, see Example 17) in 1 ml of dry tetrahydrofuran. The solution is stirred at room temperature for 2 hours then p-methoxy-benzenesulfonyl chloride (10 mg, 0.047 mmol) is added. The mixture is stirred at room temperature for 1 hour then partitioned between 5% aqueous sodium bicarbonate (1 ml) and methylene chloride (1 ml). The layers are separated and the aqueous layer extracted with methylene chloride (2 ml). The combined extracts are dried with magnesium sulfate, filtered, and evaporated under vacuum. Preparative layer chromatography of the residue on a 1.0 mm silica gel plate eluted with 3% methanol in methylene chloride affords 1-N (p-methoxy-benzene sulfonyl)-29-N-ethyl 24-methoxy-24,25-dihydro-marcfortine B which is identified by nuclear magnetic resonance and mass spectrometry.

EXAMPLE 19

29-N-ethyl-24,25-dihydro-marcfortine B

A mixture consisting of 15 mg of 5% platinum on carbon and 29-N-ethyl marcfortine B (29 mg, 0.06 mmol, see Example 5) in 1 ml of methanol is stirred vigorously under an atmosphere of hydrogen for 45 minutes. The reaction mixture is filtered through Celite ® and the filtrate is evaporated under vacuum. Preparative layer chromatography of the residue on a 0.5 mm silica gel plate eluted with 3% methanol in methylene chloride affords 29-N-ethyl-24,25-dihydro-marcfortine B which is identified by nuclear magnetic resonance and mass spectrometry.

EXAMPLE 20

29-N-methyl-marcfortine C

Potassium hydride (80 mg of a 25% oil dispersion) is added to a solution of marcfortine C (28 mg, 0.060 mmol) in 2 ml of dry tetrahydrofuran. The solution is stirred at room temperature for 2 hours then iodomethane (0.006 ml, 0.09 mmol) is added. The mixture is stirred at room temperature for 2 hours then partitioned between water (2 ml) and methylene chloride (3 ml). The layers are separated and the aqueous layer extracted with methylene chloride (2 ml). The combined extracts are dried with magnesium sulfate, filtered, and evaporated under vacuum. The residual oil, consisting of a mixture of 29-N-methyl marcfortine C, 1-N-methyl marcfortine C, and 1-N,29-N-bis-methyl-marcfortine C is chromatographed on a 1.0 mm silica gel plate eluted twice with 20% acetone in hexane. Three bands are isolated and identified by nuclear magnetic resonance and mass spectrometry as 29-N-methyl-marcfortine C, 1-N methyl-marcfortine C, and 1-N,29-N bis methyl-marcfortine C, respectively.

What is claimed is:

1. A compound having the formula:

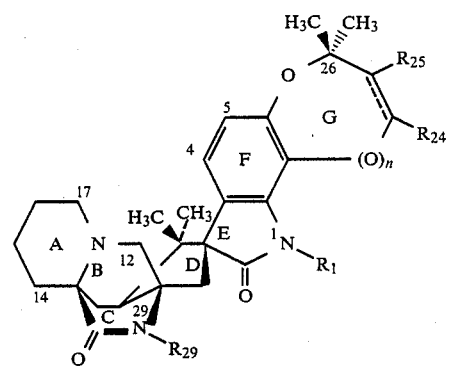

wherein:

n is 0 or 1

$R_1$ is hydrogen, lower alkyl, benzyl, lower alkanoyl, benzenesulfonyl in which the benzene ring is substituted with from 0 to 3 substituents selected from lower alkyl groups, lower alkoxy groups and halogen atoms, lower alkylamiano-carbonyl, lower alkoxy-carbonyl;

$R_{24}$ is hydrogen, halogen or lower alkoxy (provided that $R_{24}$ is other than hydrogen only if the broken line represents a single bond at the 24, 25-position), $R_{25}$ is hydrogen or halogen (provided that $R_{25}$ is other than hydrogen only if the broken line represents a single bond at the 24, 25-position);

$R_{29}$ is hydrogen, lower alkyl, alkoxyalkyl, haloalkyl, lower alkenyl, lower alkynyl, benzyl, lower alkanoyl, substituted benzenesulfonyl, lower alkylamino-carbonyl, not hydrogen or methyl if $R_1$ is hydrogen; and the broken line represents a single or double bond between carbons 24 and 25.

2. The compound of claim 1 wherein n is 1

$R_1$ is hydrogen, lower alkanoyl, substituted benzenesulfonyl, lower alkylamino-carbonyl, lower alkoxy-carbonyl;

$R_{24}$ is hydrogen, halogen or lower alkoxy (provided that $R_{24}$ is other than hydrogen only when the broken line represents a single bond at the 24,25-position);

$R_{25}$ is hydrogen or halogen (provided that $R_{24}$ is other than hydrogen only when the broken line represents a single bond at the 24,25-position);

$R_{29}$ is hydrogen, lower alkyl, alkoxyalkyl, haloalkyl, lower alkenyl, lower alkynl, benzyl, lower alkanoyl, substituted benzenesulfonyl, lower alkylamino-carbonyl, lower alkoxy-carbonyl, except that $R_{29}$ is not hydrogen or methyl if $R_1$ is hydrogen; and the broken line represents a single or double bond between carbons 24 and 25.

3. The compound of claim 2 wherein:

n is 1

$R_1$ is hydrogen, benzenesulfonyl in which the benzene ring is substituted with from 0 to 3 substitutents selected from lower alkyl groups lower alkoxy groups and halogen atoms;

$R_{24}$ is hydrogen; or lower alkoxy (provided that $R_{24}$ is other than hydrogen only when the broken line represents a single bond at the 24, 25-position);

$R_{25}$ is hydrogen;

$R_{29}$ is hydrogen, lower alkyl, alkoxyalkyl, halaoalkyl, lower alkenyl, lower alkynl, benzyl, lower alkanoyl, substituted benzenesulfonyl, lower alkylamino-carabonyl, lower alkoxy-carbonyl, except that $R_{29}$ is not hydrogen or methyl if $R_1$ is hydrogen; and the broken line represents a double bond between carbons 24 and 25.

4. The compound of claim 3 wherein
n is 1
$R_1$ is hydrogen;
$R_{24}$ is hydrogen;
$R_{25}$ is hydrogen
$R_{29}$ is lower alkyl (except methyl), alkoxyalkyl, lower alkenyl, lower alkynl, benzyl; and the broken line represents a double bond between carbons 24 and 25.

5. The compound of claim 1 wherein:
n is 0
$R_1$ is hydrogen, lower alkanoyl, benzenesulfonyl in which the benzene ring is substituted with from 0 to 3 substituents selected from lower alkyl groups, lower alkoxy groups and halogen atoms, lower alkylamino-carbonyl, lower alkoxy-carbonyl;
$R_{24}$ is hydrogen;
$R_{25}$ is hydrogen;
$R_{29}$ is hydrogen, lower alkyl, alkoxyalkyl, haloalkyl, lower alkenyl, lower alkynl, benzyl, lower alkanoyl, substituted benzenesulfonyl, lower alkylamino-carbonyl, lower alkoxy-carbonyl, except that $R_{29}$ is not hydrogen or methyl if $R_1$ is hydrogen; and the broken line represents a single or double bond between carbons 24 and 25.

6. The compound of claim 5 wherein
n is 0
$R_1$ is hydrogen;
$R_{24}$ is hydrogen;
$R_{25}$ is hydrogen;
$R_{29}$ is lower alkyl (except methyl), alkoxyalkyl, lower alkenyl, lower alkynl, benzyl; and the broken line represents a double bond between carbons 24 and 25.

7. The compound of claim 1 which is 29-N-ethylmarcfortine B.

8. The compound of claim 1 which is 29-N-allyl-marcfortine C.

9. The compound of claim 1 which is 29-N-propargyl-marcfortine B.

10. The compound of claim 1 which is 29-N-benzyl-marcfortine B.

11. The compound of claim 1 which is 29-N-methoxyethoxymethyl-marcfortine B.

12. The compound of claim 1 which is 24,25-dihydro-marcfortine A.

13. The compound of claim 1 which is 24-methoxy-24,25-dihydro-marcfortine B.

14. The compound of claim 1 which is 29-N-acetyl-marcfortine B.

15. The compound of claim 1 which is 29-N-(p-toluenesulfonyl)-marcfortine B.

16. A method for the treatment and/or prevention of helminth or anthropod infections in domesticated animals which comprises treating such animals with an effective amount of a compound of claim 1.

17. A method for the treatment of insect or nematode pests of plants which comprises treating said plants or the soil in which they grow with an effective amount of a compound of claim 1.

18. A composition useful for the treatment and/or prevention of helminth or anthropod infections of domesticated animals which is comprised of an inert carrier and a compound of claim 1.

19. A composition useful for the treatment of insect or nematode pests of plants which is comprised of an inert carrier and a compound of claim 1.

* * * * *